United States Patent [19]

Roychowdhury

[11] Patent Number: 4,816,220

[45] Date of Patent: Mar. 28, 1989

[54] DEODORANT COMPOSITION FOR ABATING THE ODOR OF ORGANIC REFUSE

[76] Inventor: Sukomal Roychowdhury, 174 Heathcote Rd., Elmont, N.Y. 11003

[21] Appl. No.: 71,981

[22] Filed: Jul. 10, 1987

[51] Int. Cl.$^4$ .............................................. A61L 9/14
[52] U.S. Cl. ...................................... 422/5; 424/76.5; 424/76.6
[58] Field of Search .................. 422/5; 424/76.5, 96.6

[56] References Cited

U.S. PATENT DOCUMENTS 4,511,552  4/1985  Cox ..................................... 422/5 X

FOREIGN PATENT DOCUMENTS 60-40057  3/1985  Japan ................................... 424/76.6
8102891  10/1981  PCT Int'l Appl. ..................... 422/5

*Primary Examiner*—Barry S. Richman
*Assistant Examiner*—Jill Johnston
*Attorney, Agent, or Firm*—Curtis, Morris & Safford

[57] ABSTRACT

A deodorant composition in concentrate form for abating the odor of organic refuse, said composition being in suitable form the application to said organic refuse in spray form, comprising:

(a) from 5 to 15% by weight of isopropanol;
(b) from 2 to 8% by weight of a glycol selected from the group consisting of propylene glycol, 1,4-butanediol, and butylene glycol;
(c) from 30 to 60% by weight of water;
(d) from 20 to 40% by weight of an emulsifying and surfactant agent selected from the group consisting of sodium lauryl sulfate, glycerol monostearate and alkyl phenoxy polyethoxy ethanol;
(e) an effective amount of a binding agent selected from the group consisting of sodium carboxymethyl cellulose, methyl cellulose, and 2-hydroxyethyl cellulose; and
(f) as an active deodorizing agent, from 5 to 15% by weight of said concentrate composition of an essential oil.

8 Claims, No Drawings

DEODORANT COMPOSITION FOR ABATING THE ODOR OF ORGANIC REFUSE

This invention relates to a deodorant composition for abating the odor of organic refuse. More specifically, this invention relates to a deodorant composition which can be sprayed on garbage and like organic refuse to control the odor thereof.

The offensive odors emanating from landfills constitute a serious environmental and social problem. The lack of suitable landfill sites has become a difficult problem for local and state authorities.

The offensive odors emanating from landfills are primarily due to microbial action in the organic refuse, i.e., restaurant and foodstuff wastes, household refuse, or any cellulosic material. Typically the microbial metabolism is greater in the warmer months and during those months communities located downwind of landfills or sewage treatment plants are seriously inconvenienced by the bad odor emanating from the landfill.

It is understood that there is a wide range of microbes which act alone or in conjunction with one another on the organic refuse. The end product of this microbial action is typically a combustible gas. The microbial action, although it does produce an unpleasant odor, also results in substantial volume reduction of the organic refuse during the decomposition process and accordingly is not without substantial benefit to the landfill.

It is recognized that one way to eliminate the odor emanating from the landfill is to inhibit the growth of the microbial population. This typically can be achieved by adding toxic substances to eliminate or at least control the growth of the microorganisms. Unfortunately, the consequence of eliminating the microorganisms is the elimination of effective bacterial action and while odor is abated there is also no reduction in time of the volume of the landfill. There is also interruption with the production of gases which has proven profitable in some landfills. Still a further disadvantage of using toxic substances to eliminate microorganisms is that toxic leachates are produced which may lead to the contamination of underground water or neighboring bodies of water.

The art has heretofore failed to eliminate the odor of landfills without disadvantageously reducing the level of microbial activity. Nontoxic masking agents have heretofore been used but have not proven to be satisfactory for the purpose.

An effective, strong, inexpensive, nontoxic masking agent has now been discovered. When applied in spray form, it completely deodorizes the landfill without any adverse effect either to the landfill, the microbial action taking place therein, the ground water, or the environment.

The composition of the invention is a composition in concentrate form, which abates the odor of the organic refuse. It comprises:

(a) from 5 to 15% by weight of isopropanol;
(b) from 2 to 8% by weight of a glycol selected from the group consisting of propylene glycol, butanediol and butylene glycol;
(c) from 30 to 60% by weight of water;
(d) from 20 to 40% of an emulsifying and surfactant agent selected from the group consisting of sodium lauryl sulfate, glycerol monostearate and alkyl phenoxy polyethoxy ethanol;
(e) an effective amount of a binding agent selected from the group consisting of sodium carboxymethyl cellulose, methyl cellulose and 2-hydroxyethyl cellulose; and
(f) as an active deodorizing agent, from 5 to 15% by weight of an essential oil.

The isopropanol serves the purpose of solubilization and dispersion of oil and stabilization of the emulsion. It also acts as an antifreeze. Desirably the composition comprises from 5 to 15% by weight of isopropanol and preferably from 8 to 10%.

The composition also contains an aliphatic glycol selected from the group consisting of propylene and butylene glycol, and 1,4-butanediol. The preferred glycols are propylene glycol and butylene glycol. These act as antifreeze and as a stabilizing agent. Desirably the composition comprises from 2 to 8% by weight of propylene glycol and preferably from 4 to 6% by weight.

The deodorant composition also includes an emulsifying and surfactant agent which serves the purpose of thoroughly dispersing the essential oils (active deodorant) so that when sprayed, the active deodorant falls uniformly on the surface of the refuse. While any effective amount of such emulsifying and surfactant agent will suffice, typically the deodorant composition in the concentrated form contains from 20% to 40% and preferably from 25% to 30% by weight of the emulsifying and surfactant agent.

While any effective amount of the binding agent will suffice, typically the deodorant composition contains from 0.1% to 1.0% by weight and preferably from 0.2% to 0.5% by weight of the binding agent.

The active deodorizing agents used in the compositions of the invention are selected from the group consisting of eucalyptus oil, lemon grass oil, and juniper berry oil. From 5 to 15% and preferably from 8 to 12% is most effective.

The product has the capacity to completely mask the offensive odor of refuse of landfills, sewage treatment plants, dairy, chicken or pig farms, or other odor producing operations. The product has no toxic or hazardous effect on the microbes of the landfill or on the environment. The concentrated product when diluted and sprayed not only neutralizes the odor but prolongs the masking effect.

The deodorant composition in concentrate form described above may be prepared as follows. The essential oils are mixed in the alcohol. An emulsifying and surfactant agent is then added to the mixture and stirred well. When a thoroughly mixed solution is obtained, the binding agent is added and the solution is mixed well again. Thereafter, propylene glycol is added and mixed. Finally, when the ingredients are mixed and show no separation, water is added and the composition is again mixed. Color and foaming agents are optionally added. Color gives an aesthetically soothing look and the foaming agents slow the leaching of the liquid from the landfill.

To apply the deodorant composition to the landfill, the composition in concentrate form is typically diluted with water from 5 to 40 times. Typically the concentrate is diluted with twenty volumes of water and the dilute solution is applied to the landfill by spray guns known in the art. If desirable, a foaming agent may be added to the concentrate or to the dilute solution to facilitate the delivery of the deodorant composition in a foam form. In foam form, the composition may be more easily applied to the surface of the landfill.

The compositions of the invention are further described in the following examples.

EXAMPLE I

A deodorant composition in concentrate form was prepared having the following composition:

|   |   | Parts By Weight Composition |
|---|---|---|
| (a) | isopropanol | 10.0 |
| (b) | propylene glycol | 5.0 |
| (c) | water | 44.0 |
| (d) | alkyl phenoxy polyethoxy ethanol (emulsifying agent) | 30.0 |
| (e) | sodium carboxymethyl cellulose (binding agent) | 1.0 |
| (f) | eucalyptus oil (7 parts), lemon grass oil (2.5 parts), and juniper berry oil (0.5 parts) (active deodorizing agent) | 10.0 |
|   | Total | 100.0 |

EXAMPLE II

A deodorant composition in concentrate form was prepared having the following composition:

|   |   | Parts By Weight Composition |
|---|---|---|
| (a) | isopropanol | 8.0 |
| (b) | propylene glycol | 6.0 |
| (c) | water | 38.4 |
| (d) | sodium lauryl sulfate (emulsifying agent) | 35.0 |
| (e) | sodium carboxy methyl cellulose (binding agent) | 0.6 |
| (f) | lemon grass oil (active deodorizing agent) | 12.0 |
|   | Total | 100.0 |

EXAMPLE III

A deodorant composition in concentrate form was prepared having the following composition:

|   |   | Parts By Weight Composition |
|---|---|---|
| (a) | isopropanol | 14.0 |
| (b) | butanediol | 4.0 |
| (c) | water | 40.5 |
| (d) | glycerol monostearate (emulsifying agent) | 26.0 |
| (e) | methyl cellulose (binding agent) | 0.5 |
| (f) | juniper berry oil (active deodorizing agent) | 15.0 |
|   | Total | 100.0 |

EXAMPLE IV

A deodorant composition in concentrate form was prepared having the following composition:

|   |   | Parts By Weight Composition |
|---|---|---|
| (a) | isopropanol | 6.0 |
| (b) | butylene glycol | 3.0 |
| (c) | water | 50.2 |
| (d) | glycerol monostearate (emulsifying agent) | 27.5 |
| (e) | 2-hydroxy ethylcellulose (binding agent) | 0.8 |
| (f) | eucalyptus oil (active deodorizing agent) | 12.5 |
|   | Total | 100.0 |

EXAMPLE IV

A deodorant composition in concentrate form was prepared having the following composition:

|   |   | Parts By Weight Composition |
|---|---|---|
| (a) | isopropanol | 9.0 |
| (b) | propylene glycol | 5.5 |
| (c) | water | 49.7 |
| (d) | alkyl phenoxy polyethoxy ethanol (emulsifying agent) | 28.0 |
| (e) | methyl cellulose (binding agent) | 0.3 |
| (f) | eucalyptus oil (active deodorizing agent) | 7.5 |
|   | Total | 100.0 |

The compositions of the invention have been found to be effective to abate, for substantial periods of time, the unpleasant odors emanating from landfills. Application of the deodorant composition does not contravene environmental considerations, does not produce leachate, and does not interfere with the microbial action of the landfill, thereby interfering with gas production from the landfill or reducing the volume thereof. The compositions of the invention can be applied to sewage facilitates as well as garbage dumps and the like.

The application of the deodorant composition to a landfill will depend in part on the concentration of the organic refuse, the ambient temperature, the chosen concentration of the deodorant composition, i.e., the extent of dilution, etc. Nevertheless, it has been found that an effective abatement of the landfill odor can be achieved if from 75 to 150 gallons of a deodorant composition as (concentrate) described in Example I are applied per acre of the landfill area. The diluted composition is sprayed on the landfill. It has been found that, subject to temperature, wind force, humidity, precipitation, and other factors, the application of the aforesaid amount of a deodorant composition will effectively abate the odor emanating from the landfill for a period of 3 to 5 days.

What is claimed is:

1. A deodorant composition in concentrate form for abating the odor of organic refuse comprising:
    (a) from 5 to 15% by weight of isopropanol;
    (b) from 2 to 8% by weight of a glycol selected from the group consisting of propylene glycol, 1,4-butanediol, and butylene glycol;
    (c) from 30 to 60% by weight of water;
    (d) from 20 to 40% by weight of an emulsifying and surfactant agent selected from the group consisting of sodium lauryl sulfate, glycerol monostearate and alkyl phenoxy polyethoxy ethanol;

(e) an effective amount of a binding agent selected from the group consisting of sodium carboxymethyl cellulose, methyl cellulose and 2-hydroxyethyl cellulose; and (f) as an active deodorizing agent, from 5 to 15% by weight of an essential oil.

2. A deodorant composition as recited in claim 1 wherein the composition contains 8 to 10% isopropanol.

3. A deodorant composition as recited in claim 1 wherein the composition contains from 4 to 6% of propylene glycol.

4. A deodorant composition as recited in claim 1 wherein the composition contains from 25 to 30% by weight of alkyl phenoxy polyethoxy ethanol.

5. A deodorant composition as recited in claim 1 wherein the composition contains from 0.1 to 1.0% by weight of sodium carboxy methyl sulfate.

6. A deodorant composition as recited in claim 1 wherein the composition contains from 8 to 12% of an essential oil selected from the group consisting of eucalyptus oil, lemon grass oil and juniper berry oil.

7. A deodorant composition in concentrate form for abating the odor of organic refuse, said composition being in suitable form for application to said organic refuse in spray form, comprising:

(a) from 8 to 10% by weight of isopropanol;

(b) from 4 to 6% by weight of a glycol selected from the group consisting of propylene glycol, 1,4-butanediol, and butylene glycol;

(c) from 30 to 60% by weight of water;

(d) from 25 to 30% of an emulsifying and surfactant agent selected from the group consisting of sodium lauryl sulfate, glycerol monostearate and alkyl phenoxy polyethoxy ethanol;

(e) from 0.1 to 1.0% by weight of a binding agent selected from the group consisting of sodium carboxymethyl cellulose, methyl cellulose, and 2-hydroxyethyl cellulose; and (f) as an active deodorizing agent, from 5 to 15% by weight of an essential oil selected from the group consisting of eucalyptus oil, lemon grass oil and juniper berry oil.

8. A method for abating the odor of organic refuse comprising the step of applying a fine spray of a deodorant composition to said organic refuse in an amount effective to abate the odor thereof, said composition comprising:

(a) from 5 to 15% by weight of isopropanol;

(b) from 2 to 8% by weight of a glycol selected from the group consisting of propylene glycol, 1,4-butanediol, and butylene glycol;

(c) from 30 to 60% by weight of water;

(d) from 20 to 40% by weight of an emulsifying and surfactant agent selected from the group consisting of sodium lauryl sulfate, glycerol monostearate and alkyl phenoxy polyethoxy ethanol;

(e) an effective amount of a binding agent selected from the group consisting of sodium carboxymethyl cellulose, methyl cellulose, and 2-hydroxyethyl cellulose; and (f) as an active deodorizing agent, from 5 to 15% by weight of said concentrate composition of an essential oil.

* * * * *